United States Patent [19]

Trompler

[11] Patent Number: 4,928,311

[45] Date of Patent: May 22, 1990

[54] NOISE LIMITING CIRCUIT FOR EARMUFFS

[76] Inventor: Lyle D. Trompler, 13906 Wickersham, Houston, Tex. 77077

[21] Appl. No.: 70,104

[22] Filed: Jul. 1, 1987

Related U.S. Application Data

[63] Continuation of Ser. No. 815,883, Jan. 3, 1986, abandoned.

[51] Int. Cl.$^5$ .............................................. A61F 11/02
[52] U.S. Cl. ...................................... 381/72; 381/74; 330/2
[58] Field of Search ........................... 381/68, 72, 74; 307/540, 546, 552, 553; 330/2

[56] References Cited

U.S. PATENT DOCUMENTS

| | | | |
|---|---|---|---|
| 3,306,991 | 2/1967 | Wood | 381/72 |
| 3,394,226 | 7/1968 | Andrews, Jr. | 381/72 |
| 3,683,130 | 8/1972 | Kahn | 381/72 |
| 3,768,028 | 10/1973 | Wolcott et al. | 330/2 |
| 3,991,272 | 11/1976 | Tarr | 381/108 |
| 4,008,440 | 2/1977 | Mizukoshi | 307/553 |
| 4,052,571 | 10/1977 | Gregory et al. | 381/68.4 |
| 4,064,362 | 12/1977 | Williams | 381/72 |
| 4,085,299 | 4/1978 | Hobrough | 381/55 |
| 4,224,470 | 9/1980 | Persson et al. | 381/72 |
| 4,406,923 | 9/1983 | Burne, III | 381/108 |
| 4,506,113 | 3/1985 | Blomley | 307/540 |
| 4,517,415 | 5/1985 | Laurence | 381/68.4 |
| 4,543,453 | 9/1985 | Brander | 381/68.4 |
| 4,629,834 | 12/1986 | Waggoner et al. | 381/74 |

FOREIGN PATENT DOCUMENTS

| | | | |
|---|---|---|---|
| 1160431 | 8/1963 | United Kingdom | 381/72 |
| 1378294 | 12/1974 | United Kingdom | 381/72 |

OTHER PUBLICATIONS

G. Marosi, "Acoustic Protector . . .", Electronics, vol. 52, No. 3, Feb. 1979, pp. 115–117.
Jung, IC OP-AMP Cookbook, 1980, pp. 232–233.
AN-72-30 (National Semiconductor) Sep., 1972.
Lancaster, CMOS Cookbook, 1979, p. 353.
National Semiconductor, Linear Data Book, 1976, LM381A (pp. 10–46).

Primary Examiner—Forester W. Isen
Attorney, Agent, or Firm—Pravel, Gambrell, Hewitt, Kimball & Krieger

[57] ABSTRACT

A protective earmuff which transmits normal sound levels and clips higher amplitude sound levels by causing an amplifier to go into saturation when the input signal is greater than a preset amount. The sound is received by a microphone, amplified and transmitted to the ear of the user by a speaker. The output of volume level is controllable independently of the clipping level. Also disclosed is a circuit allowing user control of both the clipping level and the volume level independently.

8 Claims, 4 Drawing Sheets

NOISE LIMITING CIRCUIT FOR EARMUFFS

This is a continuation of co-pending application Ser. No. 815,883, filed on Jan 3, 1986, now abandoned.

BACKGROUND OF THE INVENTION

1. Field of the Invention

The invention relates to the field of hearing protectors, especially to an earmuff hearing protector including an electrical circuit with noise limiting features.

2. Description of the Prior Art

It has long been known that a person's ears are subject to permanent damage from high volume or high intensity noises. In the past, to reduce the potential for hearing loss, various forms of ear protectors such as earmuffs or ear plugs have been utilized. One common problem with such noise suppressors was that the wearer could not hear normal level sounds such as conversation, alarms, or other aural signals.

To solve this problem, earmuffs or noise limiters were provided with means for receiving and amplifying non-harmful sounds which nonetheless provided some dampening of harmful, more intense noise. U.S. Pat. No. 3,306,991 disclosed a system having a microphone, a pre-amplifier, a limiting amplifier and a speaker enclosed in a set of earmuffs such that the user could hear normal level sounds but sounds over a certain level would be limited. The patent disclosed the concept of limiting sound levels but did not show any particular electrical circuit configurations to perform this function beyond mentioning that an automatic gain control system could be used.

U.S. Pat. No. 3,394,226 disclosed a hearing protector which included an input audio filter to remove undesirable audio frequencies from the sounds received by a microphone thereby removing potentially harmful portions of the audio spectrum.

U.S. Pat. No. 3,683,130 disclosed a system which included a series of filter networks to shape the frequency response of the amplifier and reverse-biased clipping diodes to clip signals above a desired amplitude. Another diode clipping circuit was disclosed in U.S. Pat. No. 4,224,470.

U.S. Pat. No. 4,064,362 disclosed an automatic gain control system to limit the output signal level from the microphone and thereby the signal level transmitted by the speaker contained in the headphone system.

It is desirable that the electrical circuitry performing the frequency filtering and noise limiting functions be simple. The simplicity reduces the cost and the size of the unit, allowing the earmuff to be used more widely in cost sensitive and space sensitive environments. All of the prior art devices used separate circuit elements to perform the limiting function, thereby increasing their size and cost.

SUMMARY OF THE INVENTION

In contrast to the prior art, the present invention provides a simplified noise limiting system wherein any high amplitude sounds are clipped or limited without the need for additional diodes or automatic gain control circuitry. The clipping or noise limiting function is provided by designing the initial amplification stage following the microphone so that when the external noise levels reach a desired level the input amplifier is in saturation and can no longer amplify the received sound signal. This amplified and possibly clipped signal is then divided by a variable amount and amplified to drive an output transducer or speaker. Speaker volume control is achieved by varying the voltage divider to the second stage of amplification.

In an alternate embodiment of the invention, multiple stages of amplification are provided to the input signal with a feedback resistor connecting the output of the final amplification stage to the input of the initial amplification stage. The feedback resistor value determines overall gain and can be used to set the clipping level. The amplification stages are comprised of low power consumption parts, allowing extended use from a single battery. The volume control in this embodiment is performed by varying a resistor in series with the speaker and thereby varying the voltage level of the speaker.

A third embodiment of the invention places a variable resistor in the feedback loop of the amplifier, thereby allowing a variable clipping level which can be adjusted to suit the individual user and the individual ambient noise environment.

DETAILED DESCRIPTION OF THE ALTERNATE EMBODIMENT

Figure 1:
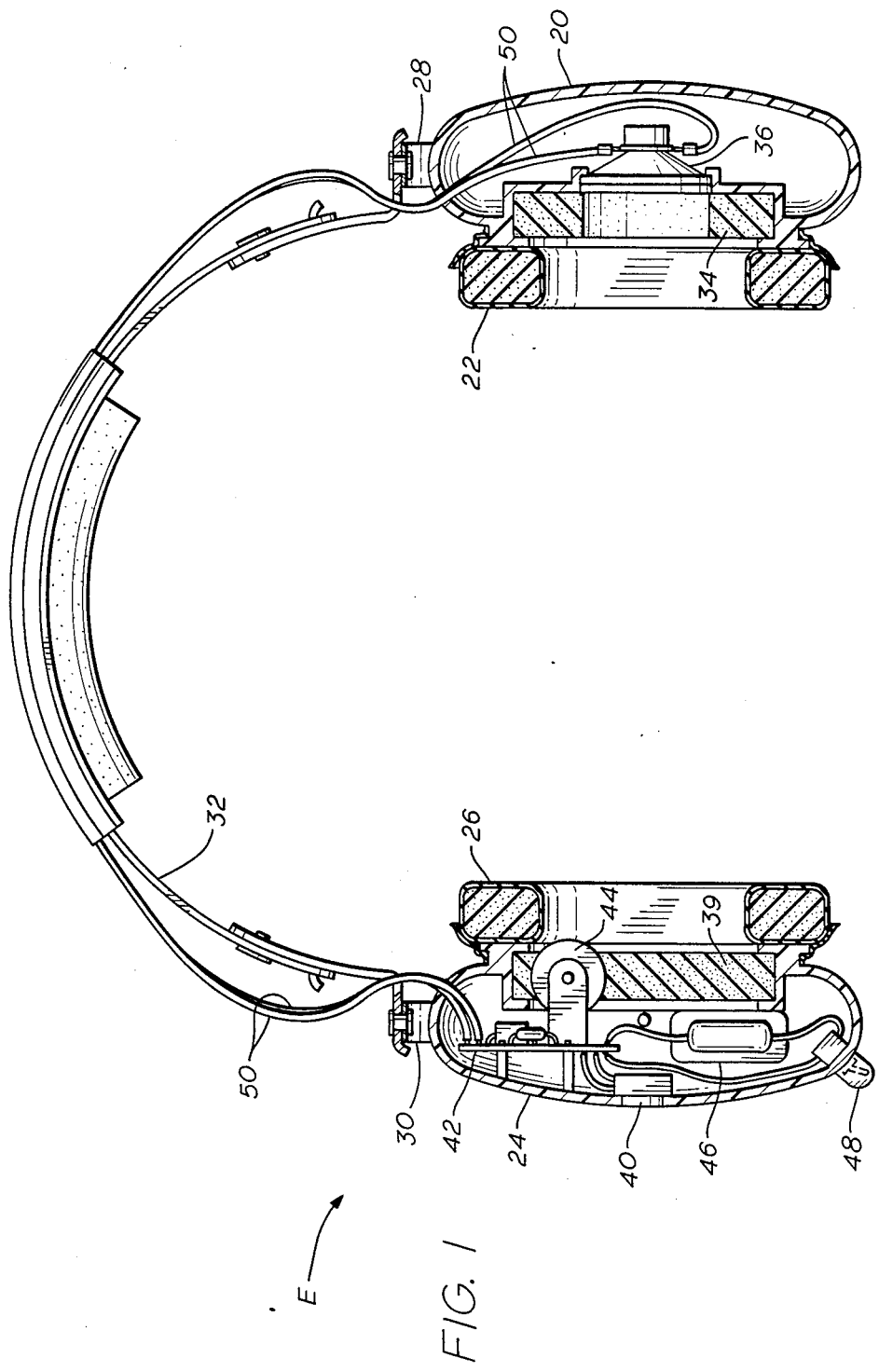
FIG. 1 is cross-sectional view of a pair of earmuffs according to the present invention.

Referring to FIG. 1, the letter E generally represents a pair of earmuffs according to the present invention. The earmuffs E are comprised of molded ear cup 20 and 24 with associated foam rolls 22 and 26, bails 28 and 30 connected to the ear cups 20 and 24 and connected to the head band 32. Contained inside one ear cup 20, is an inner foam liner 34 and a speaker 36. Mounted inside the second ear cup 24 is a microphone 40, a circuit board 42 containing various components, a volume control 44 which protrudes through an inner foam liner 39, a battery 46 to provide power to the electrical devices and a power switch 48. Speaker wires 50 are connected from the circuit board 42 to the speaker 36 to enable the electrical components to drive the speaker 36.

Figure 2:
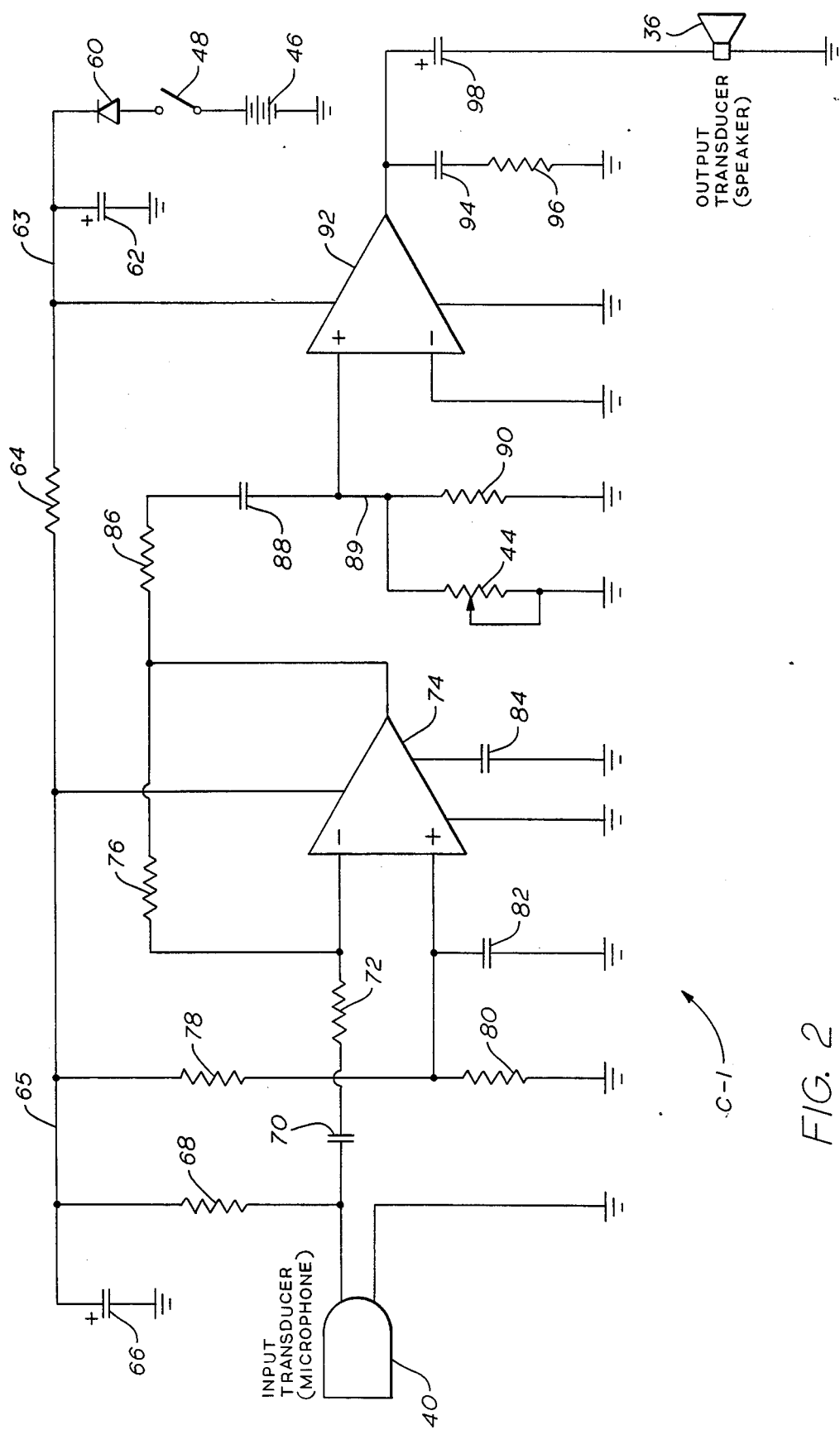
FIG. 2 is schematic diagram of a circuit according to the present invention.

One embodiment of the electrical circuitry associated with the present invention is shown in FIG. 2 and designated generally as C-1. Electrical power to this circuit is supplied by battery 46 which is connected between ground and the power switch 48. The power switch 48 is connected in series with a blocking diode 60 to prevent damage to the electrical components should the battery 46 be installed in a reverse polarity configuration. A resistor 64 is connected in series with the blocking diode 60. This produces a high current bus 63 between the diode 60 and the resistor 64 and a sensitive bus 65 after the resistor 64. The buses are split to provide decoupling and isolation between the sensitive or low current portion of the circuit C-1 and the higher current output section of the circuit C-1. A capacitor 62 is connected between the high current bus 63 and ground and a capacitor 66 is connected between the sensitive bus 65 and ground. These capacitors provide filtering to the respective bus.

The input transducer or microphone 40 is connected between ground and resistor 68 which is in turn connected to sensitive bus 65. The microphone 40 is an electret-type microphone having an internal field effect transistor. A resistor 68 acts as the load resistor for the field effect transistor in the microphone 40 and the junction between the microphone 40 and the load resistor 68 is the output of the microphone 40.

The microphone output is connected to the inverting input of an operational amplifier 74 through the series combination of a capacitor 70 and a resistor 72. The capacitor 70 provides direct current isolation between the microphone 40 and the amplifier 74 so that only the alternating current portions of the signal are amplified and the clipping is done uniformly on both halves of the waveform. The combination of resistor 68, capacitor 70 and resistor 72 are used to establish portions of the desired frequency response of the circuit C-1.

A resistor 76 is connected to the output of the amplifier 74 and to the inverting input of the amplifier 74. In this configuration, resistors 72 and 76 determine the gain of the amplifier 74. This gain is set such that all input signals received from the microphone 40 above a certain amplitude will cause the amplifier 74 to saturate and thus clip the output signal. By properly setting the gain of this circuit in conjunction with the output voltage characteristics of the microphone 40, the clipping level can be set such that normal conversational sound levels are amplified with no clipping but high amplitude noises such as gun shots or other loud sounds are clipped and limited to safe levels.

In this manner the maximum sound pressure transmitted to the user's ears is limited. In the illustrated embodiment a capacitor 84 is used to provide the frequency roll-off compensation for the amplifier 74. A resistor divider network comprising resistors 78 and 80 is connected between the sensitive bus 65 and ground and the junction of the two resistors 78 and 80 is connected to the non-inverting input of the amplifier 74. Also connected between the non-inverting input of the amplifier 74 and ground is a capacitor 82. The resistors 78 and 80 and the capacitor 82 provide a reference supply to the amplifier 74.

Connected in series between output of the amplifier 74 and ground are a resistor 86, a capacitor 88 and the volume control 44. In parallel with the volume control 44 is a resistor 90. The node 89 between the capacitor 88, the volume control 44 and the resistor 90 is connected to the non-inverting input of an audio amplifier 92. This network of resistors 86 and 90, the volume control 44 and the capacitor 88 act as a voltage divider network to set the proper input voltage to the audio amplifier 92. The audio amplifier 92 is a fixed gain audio amplifier, allowing simplification of the circuit design and reduction in the part count. Appropriately adjusting the volume control 44 changes the resistance of the volume control 44 and the voltage divider ratio to increase or decrease the voltage at node 89, thereby changing the output level of amplifier 92. This divider network also provides additional control of the frequency response characteristics of the circuit.

Capacitor 94 and a resistor 96 are connected in series between the output of the audio amplifier 92 and ground to stabilize the amplifier according to the manufacturer's specifications. A capacitor 98 is connected between the output of the audio amplifier 92 and the speaker 36. The speaker 36 is connected between the capacitor 98 and ground. The capacitor 98 provides direct current decoupling for speaker 36 and is a third location for setting the frequency response characteristics of the circuit C-1. The desirable overall frequency response of circuit C-1 is set by properly adjusting the three networks to provide a band width from 300 Hz to 6000 Hz. This frequency response limits the more damaging audio frequencies and passes sufficient portions of signals in the human speech bandwidth to allow clearly intelligible speech.

Figure 3:
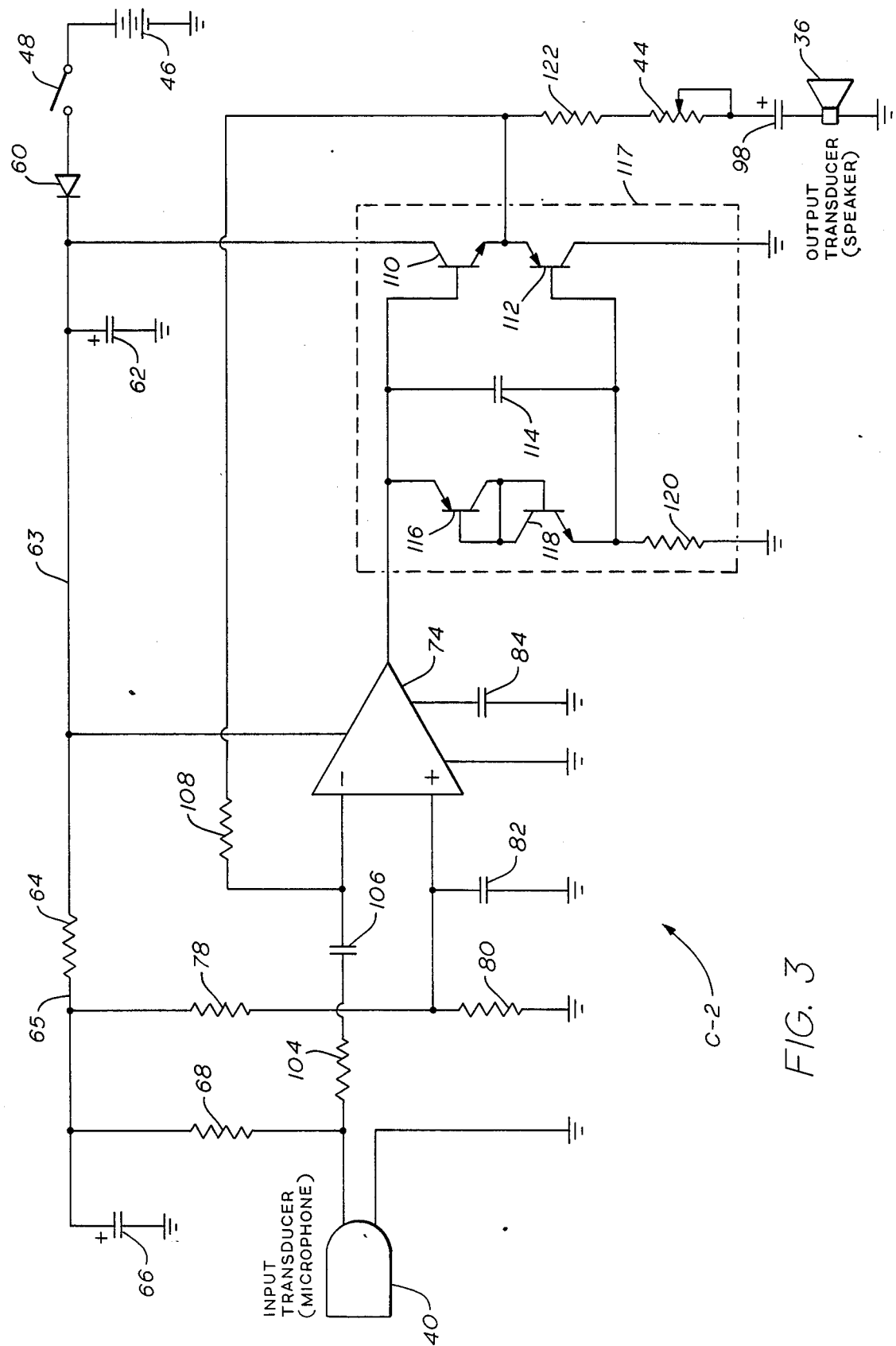
FIG. 3 is schematic diagram of a circuit according to the present invention.

FIG. 3 displays an alternate embodiment C-2 of the circuit having a reduced current drain and therefore an extended battery life. Circuit C-2 is similar to circuit C-1 in many respects. In the circuit C-2, the second amplifier 92 of circuit C-1 has been replaced by an emitter follower class B amplifier stage 117 and the feed back loop is around both amplifier 74 and the transistor amplification stage. Additionally, the volume control 44 is in series with the speaker 36. In circuit C-1 the power supply to amplifier 74 is connected to the sensitive bus 65 while the power supply connection for the audio amplifier 92 is connected to the high current bus 63. This is because the audio amplifier 92 is a relatively high current device and amplifier 74 is a low current device. In circuit C-2 the power supply to amplifier 74 is connected to the high current bus 63 because the final drive stage is sufficiently low power that there is no appreciable need for isolation between the two gain stages. This allows for improved isolation between the microphone 40 and the amplification stages.

As indicated above the amplification gain of circuit C-2 is controlled differently than that of circuit C-1. The output of amplifier 74 is connected to a emitter follower transistor amplifier stage 117. The output of amplifier 74 is connected to the base of an output NPN transistor 110. The collector of the output NPN transistor 110 is connected to the high current bus 63 and the emitter connected to the output of the transistor amplifier stage 117. A PNP transistor 112 has its emitter connected to the emitter of the output NPN transistor 110 and its collector connected to ground. The base of the output PNP transistor 112 is connected to one lead of a capacitor 114 with the other lead of the capacitor 114 connected to the base of the output NPN transistor 110. The capacitor 114 stabilizes the alternating current voltage appearing at the bases of the output transistors 110 and 112.

Also connected between the bases of the output transistors 110 and 112 is a pair of transistors coupled to output transistors 110 and 112 so that the bias of the output transistors 110 and 112 does not shift with a temperature change. The emitter of a PNP transistor 116 is connected to the output of amplifier 74. There is a common connection between the bases of bias PNP transistor 116 and a bias NPN transistor 118 and the collectors of the bias transistors 116 and 118. The emitter of the bias NPN transistor 118 is connected to the base of the output PNP transistor 112. In this configuration the bias transistors 116 and 118 are in a conducting configuration and because the bias PNP transistor 116 is the same type of transistor as the output PNP transistor 112 and the bias NPN transistor 118 is the same type of transistor as the output NPN transistor 110, the voltage across the bias transistor pair 116 and 118 follows the voltage across the emitters of the output transistors 110 and 112. This reduces the temperature variance of the bias of the output transistors 110 and 112. Connected between the base of the output NPN transistor 112 and ground is bias resistor 120. This bias resistor 120 is used to set the bias currents of the transistors for proper operation.

Connected between the output of the transistor amplification stage 117 and the inverting of input amplifier 74 is the feedback resistor 108. Proper selection of this feedback resistor 108 allows the output voltage level of the transistor amplifier stage 117 to clip when the input signal received from the microphone 40 is above a certain level which corresponds to a sound pressure level capable of causing permanent damage. The clipping occurs because the amplifier stages have reached the limits of their output voltage as defined by the power supply and therefore have saturated. Therefore, the circuit C-2 clips in a manner similar of that of C-1 by clipping any external sound amplitude levels greater than the preset amount. This allows normal conversation levels to be transmitted without clipping and yet the high amplitude sounds are clipped and restrained to a non-damaging level.

Connected between ground and the output of transistor amplifier stage 117 is a series combination of a resistor 122, the volume control 44, capacitor 98 and the speaker 36. Volume control in this configuration is achieved by varying the resistance of the volume control 44 which in turn varies the voltage applied to the speaker 36. The resistor 122 is present to prevent hazardous volume levels from the speaker 36 should the volume control 44 be set to a resistance value too low or short out. Thus resistor 122 sets the maximum volume levels of the combination.

Figure 4:
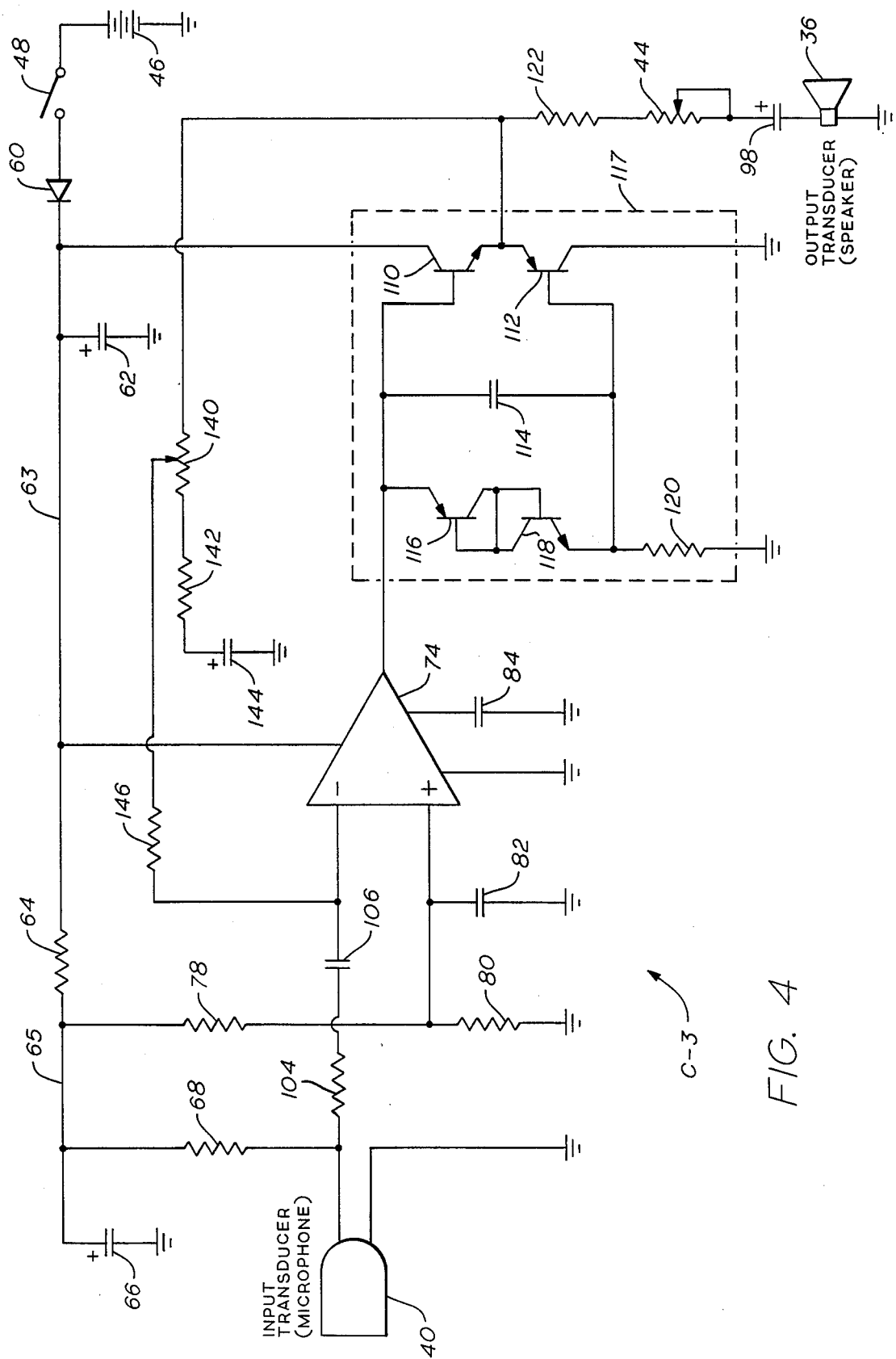
FIG. 4 is schematic diagram of a circuit according to the present invention.

Circuits C-1 and C-2 are similar in that the clip or saturation level is fixed by various components installed in the system and is not user adjustable for a given environment. Circuit C-3 shown in FIG. 4 allows the user to vary both the clip level and the volume level of the circuit independently. Circuit C-3 is a modification of circuit C-2 with the feedback resistor 108 being replaced by a variable circuit network to accomplish the variable clip level feature. A series connection of a potentiometer 140, a resistor 142 and a capacitor 144 is connected between the output of the transistor amplifier stage 117 and ground. The wiper of the potentiometer 140 is connected to a resistor 146 which is in turn connected to the inverting input of amplifier 74. Therefore, changing the position of the wiper of the potentiometer 140 varies the voltage feedback to amplifier 74 which in turn varies the gain of the two amplification stages. By adjusting the potentiometer 140 the amplification of the two stages will change and therefore the input signal required from microphone 40 to cause saturation and therefore clipping of the amplifier stages will be changed. This allows the user to tailor the circuit to individual preferences and individual environments. This is useful when the user moves from one environment to another with the noise characteristics of the environment changing such that one environment has a relatively wide bandwidth large amplitude signal and the second environment has a generally lower average signal with only occasionally high amplitude peaks. A proper adjustment in the lower average noise environment is obtained by setting the clipping level at a relatively lower amplitude and increasing the volume level thereby allowing the user to better hear the environment and yet not be endangered by any loud sounds.

The foregoing disclosure and description of the invention are illustrative and explanatory thereof, and various changes in the size, shape and materials, as well as in the details of the illustrated construction may be made without departing from the spirit of the invention.

What is claimed is:

1. A noise limiting circuit for earmuffs, comprising:
a voltage source;
a microphone for receiving sound waves and producing a microphone output signal in response thereto;
amplifier means adapted to receive and amplify said microphone output signal and connected to said voltage source;
said amplifier means including an input terminal, an amplifier circuit, and an output terminal;
said amplifier means further including gain control means for providing said amplifier means with substantially constant circuit gain as the magnitude of the microphone output signal varies from zero to a level which saturates said amplifier circuit;
said gain control means comprising means for providing substantially constant feedback resistance between said amplifier means output and input terminals, wherein said feedback resistance is selected so as to provide saturation of said amplifier circuit when the input signal level from said microphone exceeds normal conversational levels;
said microphone output signal being coupled to said amplifier means input terminal by a direct path;
speaker means for producing sound waves in response to an electrical signal; and
volume control means connected between said amplifier means output terminal and said speaker means for dividing said amplifier means output signal so that when said amplifier circuit is saturated said signal provided to said speaker means is at a level which causes said speaker means to produce a safe level of sound waves.

2. The circuit of claim 1, wherein said volume control means is a voltage divider of the amplified signal and said speaker means comprises an audio speaker for producing sound waves and audio amplifier means for amplifying the divided amplified signal and for driving said audio speaker.

3. The circuit of claim 1, further comprising filter means for filtering said microphone output signal to reduce the amplitude of frequency components outside of a predetermined audio frequency range.

4. The circuit of claim 1, wherein said substantially constant feedback resistance is adjustable by a user within preset limits.

5. A noise limiting circuit for earmuffs, comprising:
a voltage source;
a microphone for receiving sound waves and producing a microphone output signal in response thereto;
amplifier means adapted to receive and amplify said microphone output signal and connected to said voltage source;
said amplifier means including an input terminal, an amplifier circuit, and an output terminal;
said amplifier means further including gain control means for providing said amplifier means with substantially constant circuit gain as the magnitude of the microphone output signal varies from zero to a level which saturates said amplifier circuit;
said gain control means comprising means for providing substantially constant feedback resistance between said amplifier means output and input terminals, wherein said feedback resistance is selected so as to provide saturation of said amplifier circuit when the input signal level from said microphone exceeds normal conversational levels;
speaker means for producing sound waves in response to an electrical signal; and volume control means connected between said amplifier means output terminal and said speaker means for dividing said amplifier means output signal so that when said amplifier circuit is saturated said signal provided to said speaker means is at a level which causes said speaker means to produce a safe level of sound waves.

6. The circuit of claim 5, wherein said substantially constant feedback resistance is adjustable by a user within preset limits.

7. The circuit of claim 5, wherein said volume control means is a voltage divider of the amplified signal and said speaker means comprises an audio speaker for producing sound waves and audio amplifier means for amplifying the divided amplified signal and for driving said audio speaker.

8. The circuit of claim 5, further comprising filter means for filtering said microphone output signal to reduce the amplitude of frequency components outside of a predetermined audio frequency range.

* * * * *